United States Patent [19]

Zamierowski

[11] Patent Number: 4,969,880
[45] Date of Patent: Nov. 13, 1990

[54] WOUND DRESSING AND TREATMENT METHOD

[76] Inventor: David S. Zamierowski, 8500 Reinhardt, Leawood, Kans. 66206

[21] Appl. No.: 332,699

[22] Filed: Apr. 3, 1989

[51] Int. Cl.$^5$ ............................................. A61F 13/00
[52] U.S. Cl. ...................................... 604/305; 604/180
[58] Field of Search ............... 604/174, 175, 176, 179, 604/180, 304, 305, 307, 313, 26, 49; 128/DIG. 26, 156, 155

[56] References Cited

U.S. PATENT DOCUMENTS

| | | | |
|---|---|---|---|
| 3,367,332 | 2/1968 | Groves | 604/305 |
| 3,682,180 | 8/1972 | McFarlane | 604/174 |
| 4,080,970 | 3/1978 | Miller | 604/174 |
| 4,261,363 | 4/1981 | Russo | 604/174 |
| 4,275,721 | 6/1981 | Olson | 604/180 |
| 4,373,519 | 2/1983 | Errede et al. | 128/156 |
| 4,525,166 | 6/1985 | Leclerc | 604/313 |
| 4,543,100 | 9/1985 | Brodsky | 604/180 |
| 4,605,399 | 8/1986 | Weston et al. | 604/305 |
| 4,743,232 | 5/1988 | Kruger | 604/180 |

Primary Examiner—C. Fred Rosenbaum
Assistant Examiner—Kathleen A. Daley
Attorney, Agent, or Firm—Litman McMahon & Brown

[57] ABSTRACT

A wound dressing includes a cover membrane comprising a semi-permeable material with an adhesive-coated skin contact surface. An opening is formed in an interior portion of the membrane. An intermediate layer of material may be placed between the wound and the membrane contact surface for either absorbing fluids from the wound, e.g. with a hydrocolloid or hydrophilic material, or for passing such fluids to the opening with a synthetic material, e.g. rayon. A tube includes a proximate end fluidically communicating with the wound through the membrane opening. A distal end of the tube is adapted for connection to a suction source for draining the wound or fluid source for introducing liquid medication to the wound. Both evacuation and introduction can be either active or passive. A wound treatment method is also disclosed.

21 Claims, 2 Drawing Sheets

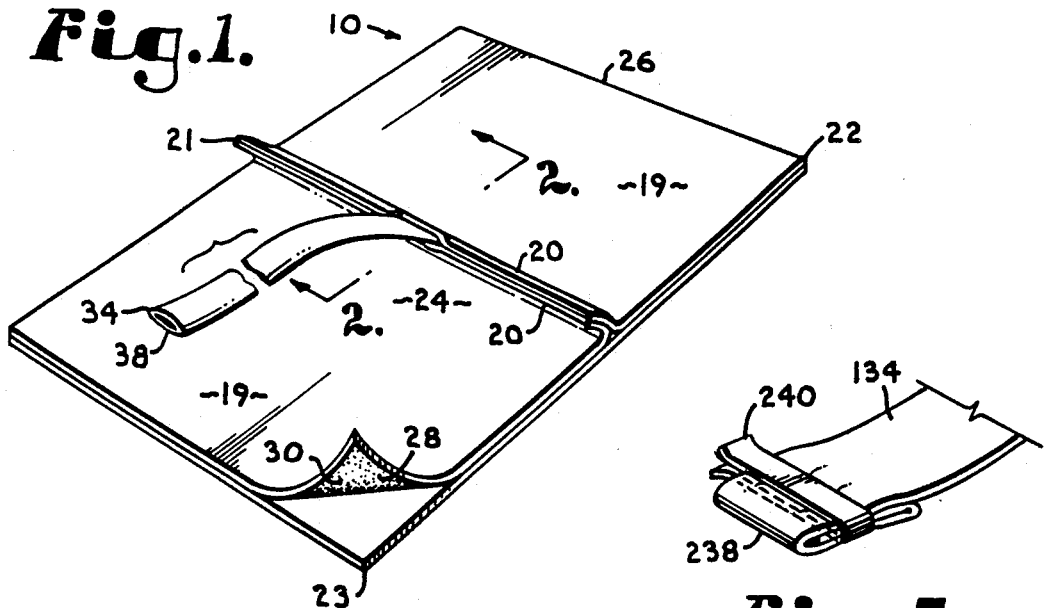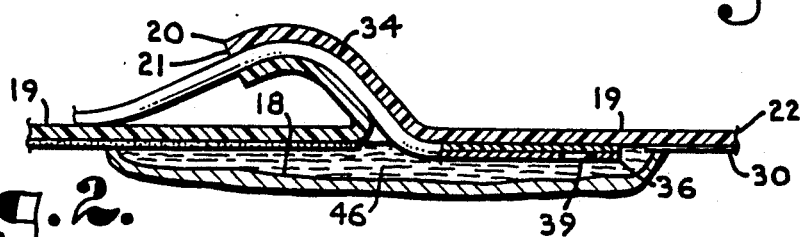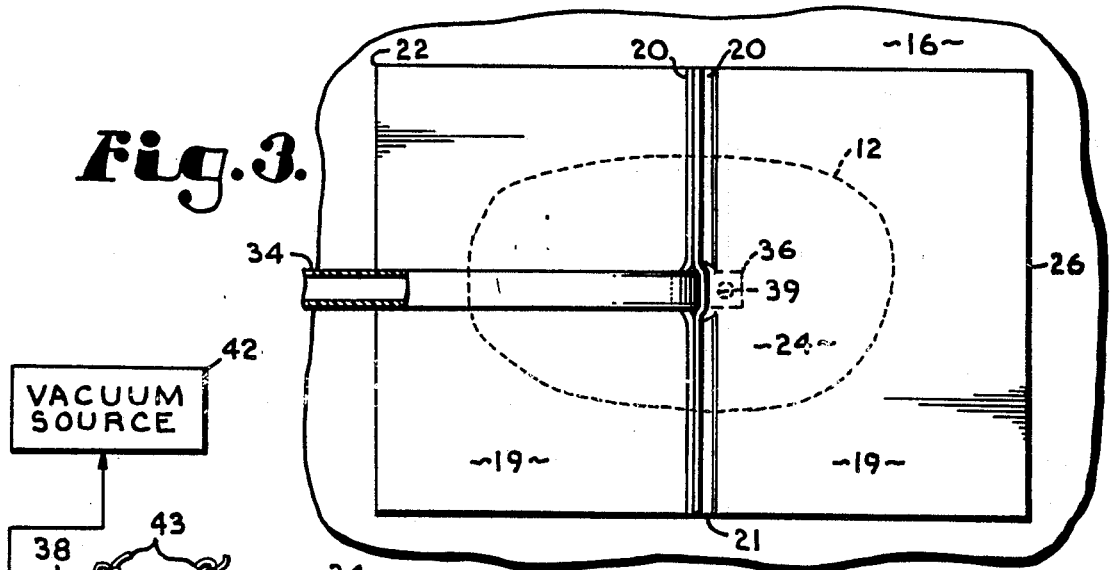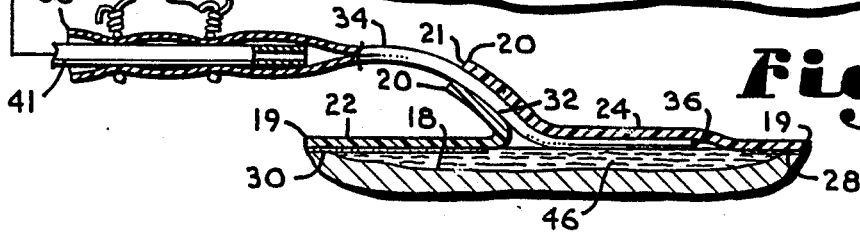

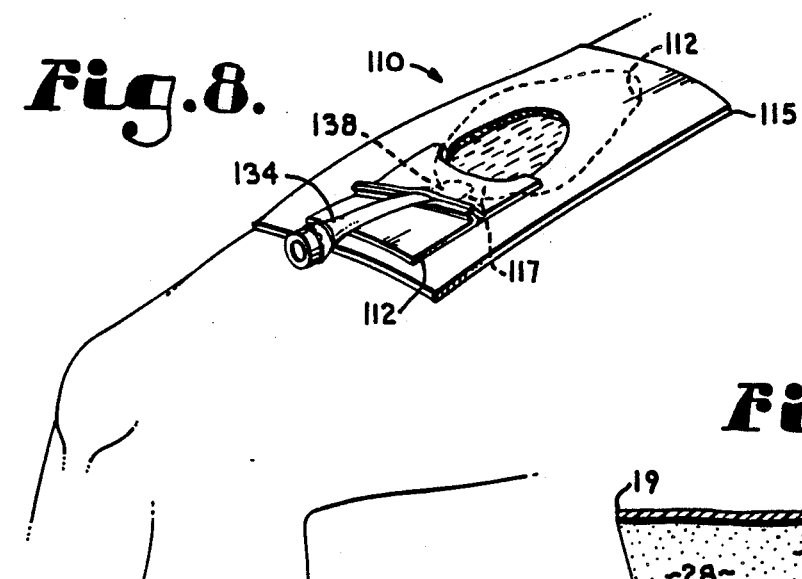
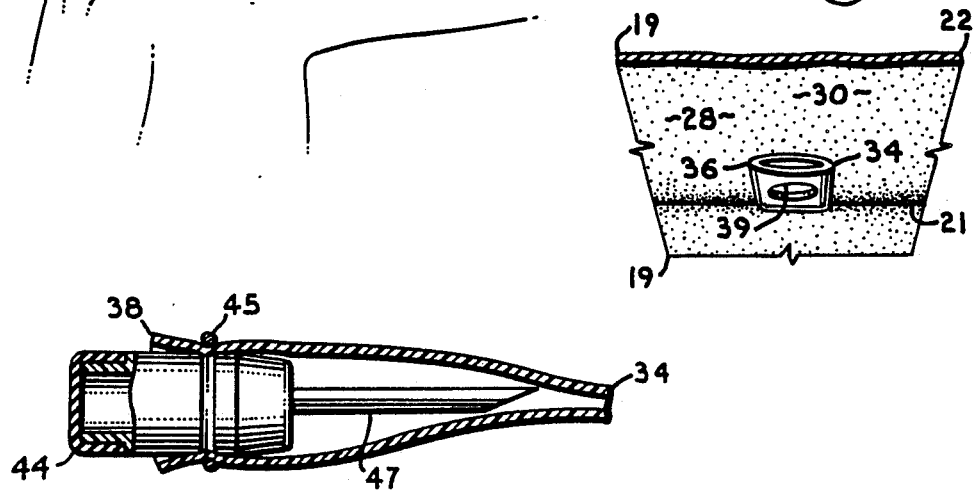
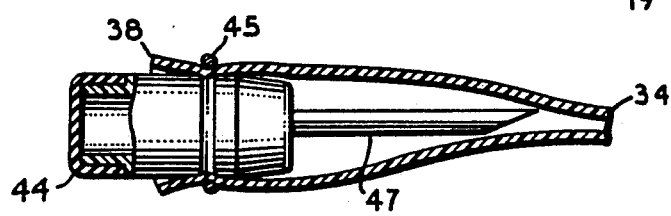
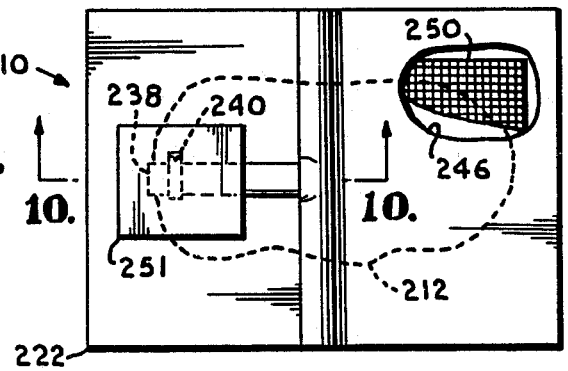
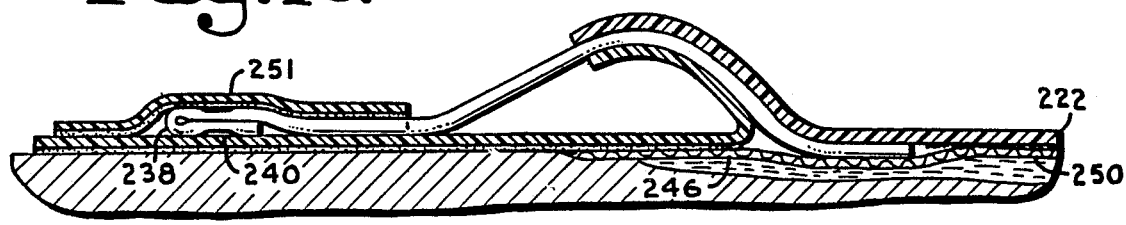

WOUND DRESSING AND TREATMENT METHOD

BACKGROUND OF THE INVENTION.

1. Field of the Invention

The present invention relates generally to wound dressings and treatment methods, and in particular to a wound dressing adapted for both introducing and evacuating fluids.

2. Description of the Prior Art.

Wound dressings are typically applied over various types of wounds to promote healing and to reduce the risk of infection. Although various types of dressing materials have been successfully employed, membranes comprising semi-permeable materials are often preferred because they can increase patient comfort and lower the risk of infection. Semi-permeable membranes generally pass moisture vapors, but are generally impervious to liquids. Thus, they can promote healing by permitting a wound site to "breathe".

However, a problem can arise with semi-permeable membranes when they are placed over draining wounds because they tend to retain fluid. For example, surgical wounds often tend to drain for a post-operative period of about forty-eight hours. The fluid that can accumulate under such a semi-permeable membrane during a draining period can macerate the underlying tissue, cause infection and otherwise inhibit healing. A procedure for alleviating this problem involves periodically piercing the membrane, draining the accumulated fluids and resealing the membrane opening. However, such a procedure is time-consuming for health care professionals and, unless it is conducted at relatively frequent intervals, can be relatively ineffective in dealing with the problems associated with trapped fluid accumulation. Other procedures which involve opening or changing wound dressings tend to have problems associated with exposing a wound to a greater risk of infection and can be uncomfortable for patients.

Another disadvantage with many previous wound dressings is that they are not designed to accommodate the introduction of various liquid medications, such as antibiotics and growth factor solutions. The application of growth factor solutions may be particularly important in the regeneration of skin graft donor sites.

Heretofore there has not been available a wound dressing apparatus and method with the advantages and features of the present invention.

Summary of the Invention

In the practice of the present invention, a wound dressing is provided which includes a semi-permeable membrane for covering a wound site. The membrane may include an interior portion with an opening and a skin contact surface with an adhesive coating. A tube or sheath is adapted for fluidically communicating with the wound site through the membrane opening and includes a proximate end which extends through the membrane opening and a distal end. The tube distal end is adapted for connection to a liquid medication source for introducing liquid medication to the wound site or a suction source for evacuating fluid therefrom. An intermediate layer of material can be applied between the wound and an interior portion of the cover membrane.

In the practice of the treatment method of the present invention, the intermediate layer of material can be applied to the wound site and the cover membrane is placed thereover. The cover membrane can be releaseably, adhesively fastened to the skin around a periphery thereof. A tube fluidically communicates with the wound through an opening in the membrane. Fluids from a draining wound can be evacuated through the tube and liquid medication can be introduced through the tube to the wound site. The fluid evacuation and the medication introduction steps of the method can each be accomplished both actively and passively.

Objects of the Invention

The principle objects of the present invention include: to provide a wound dressing; to provide such a dressing which promotes the evacuation of drained fluids; to provide such a dressing which permits the introduction of liquid medications; to provide such a dressing which includes a semi-permeable membrane for releaseable, adhesive attachment to the skin surface surrounding a wound; to provide such a dressing which protects against infection; to provide such a dressing which promotes healing; to provide such a dressing which is economical to manufacture, efficient in operation, capable of a long operating life and particularly well adapted for the proposed usage thereof; and to provide a wound treatment method.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

Brief Description of the Drawings

FIG. 1 is a top perspective view of a wound dressing embodying the present invention.

FIG. 2 is an enlarged, vertical, cross-sectional view of the dressing taken generally along line 2-2 in FIG. 1.

FIG. 3 is a top plan view of the dressing.

FIG. 4 is an enlarged, fragmentary, bottom perspective view of the dressing, particularly showing a proximate end of the tube.

FIG. 5 is an enlarged, fragmentary, top perspective view of the dressing, particularly showing a tube closure clip.

FIG. 6 is an enlarged, fragmentary, vertical, cross-sectional view of the dressing, particularly showing the tube connected to a vacuum source.

FIG. 7 is an enlarged, fragmentary, vertical, cross-sectional view of the dressing, particularly showing a resealable injection port mounted on a distal end of the tube.

FIG. 8 is a top perspective view of a wound dressing comprising a first modified embodiment of the present invention.

FIG. 9 is a top plan view of a wound dressing comprising a second modified embodiment of the present invention with an intermediate material layer between the wound site and a cover membrane.

FIG. 10 is an enlarged, fragmentary, vertical, cross-sectional view of the second modified wound dressing embodiment, taken generally along line 10-10 in FIG. 9.

Detailed Description of the Preferred Embodiments

I. Introduction and Environment.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 10 generally designates a wound dressing embodying the present invention. The dressing 10 is adapted for protecting and treating a variety of wounds, such as that shown at 12. Without limitation on the generality of the useful applications of the present invention, the dressing 10 may be applied over burns, cuts, scrapes and ulcers of various types, e.g. diabetic, decubitus, peripheral vascular disease, venous stasis and trauma ulcers.

Skin ulcers are a common problem among many diabetics, and are often brought on by poor blood circulation and nerve damage associated with diabetes. The treatment of such ulcers often involves grafting skin from a relatively healthy donor site to an ulcerous wound site. Split thickness surgical skin graft techniques may be employed to obtain skin grafts from donor sites that can then heal spontaneously. Full thickness skin grafts, on the other hand, generally require closure of the donor site. It will be appreciated from the following description that the wound dressing and treatment method of the present invention is particularly well adapted for the protection and regeneration of skin graft donor sites by providing a single dressing which facilitates both fluid drainage and growth factor introduction.

The wound site 12 is surrounded by healthy skin 16. A fibrin layer 18 forms at the wound site 12 from fibrinogen by the action of thrombin and the clotting of blood (FIGS. 2 and 6). Surgical wounds, including those associated with skin grafts, normally drain fluid. The fluid drainage from a surgical wound is generally heaviest during a post-operative period of about forty-eight hours.

II. Wound Dressing 10.

The wound dressing 10 generally comprises a cover membrane 22 with an interior portion 24 surrounded by a perimeter 26. The membrane 22 includes a skin contact surface 28 with an adhesive coating 30. The membrane 22 preferably comprises a breathable semi-permeable material characterized by an ability to pass moisture vapors and an imperviousness to liquids. The adhesive coating 30 should likewise be semi-permeable. Such membrane materials are commercially available, an example being material referred to as "Tagoderm", which is available from the 3M (Minnesota Mining and Manufacturing) Company of St. Paul, Minn. Other semi-permeable materials are available and can be successfully employed with the present invention. A protective backing 23 is placed over the adhesive coating 30 on the membrane skin contact surface 28 until the membrane 22 is ready for application.

The membrane 22 comprises a pair of panels 19 with inner, upturned edges 20 which can be adhesively joined together to form a seam 21 which extends transversely across the membrane 22 and projects generally upwardly therefrom. The panels 19 can be secured together at the seam 21 by the adhesive coating 30 to form the seam 21.

A tube or sheath 34 includes a proximate end 36 located under the membrane 22 and a distal or free end 38. The tube 34 can be inserted through the seam 21 which forms an opening 32 between the panel edge strips 20 at approximately the center of the membrane 22. A relatively short length of the tube 34 adjacent to its proximate end 36 is shown under the membrane 22, but greater lengths of the tube 34 could be placed under the membrane 22. As shown in FIG. 5, the tube proximate end 36 is open, and adjacent to the proximate end 36 an opening is formed. Preferably the tube opening 39 projects downwardly, i.e. away from the membrane skin contact surface 28. The short length of the tube 34 which is located under the membrane 22 can be releaseably secured to the skin contact surface 28 by the adhesive coating 30, preferably with the tube opening 39 facing downwardly.

The tube 34 can comprise, for example, a flexible, plastic tube of the type that is commonly used as a percutaneous sheath for intravenous treatments. Such sheaths are commercially available from Aero International, Inc. of Reading, Pa.

At its distal end 38, the tube 34 is adapted for: (1) closure with a variety of suitable closure devices; (2) connection to various active and passive fluid collection devices for draining and evacuating fluid from the wound site; and (3) connection to various fluid source devices for actively and passively introducing fluid to the wound site.

FIG. 5 shows a bifurcated clip 40 for releaseably closing and sealing the tube distal end 38, which is folded upon itself as shown.

FIG. 6 shows a vacuum tube end 41 inserted in the tube distal end 38 and secured therein by ties or ligatures 43. The vacuum tube 41 fluidically communicates with a suction or vacuum source 42 for actively draining fluid from the wound site. The suction or vacuum source 42 may comprise a relatively simple, hand-actuated bulb or bellows, or it may comprise a more sophisticated motorized pump which can be actuated at predetermined time intervals or in response to wound site conditions such as an accumulation of fluid under the membrane 22.

FIG. 7 shows an injection port 44 sealed to the tube distal end 38 by a band 45. The injection port 44 includes a sleeve 47 which can extend into the tube 34 to protect it from needle puncture. The injection port 44 can be of the type which is designed for reuse and which automatically reseals after being punctured by a syringe needle. It will be appreciated that a wide variety of devices can be employed for connecting the tube distal end 38 to various liquid medication sources.

III. Treatment Method.

According to the treatment method of the present invention, the protective backing 23 is removed from the membrane contact surface 28 to expose the adhesive coating 30 and the membrane 22 is placed over a wound site 12 with its contact surface 28 down. The membrane perimeter 26 is pressed against the healthy skin 16 surrounding the wound site 12 to preferably form a relatively liquid-tight adhesive bond therebetween. Various adhesive preparations are commercially available for supplementing the bonding action of the adhesive coating 30 in bonding the membrane contact surface 28 to the healthy skin 16. The membranes 22 may be provided in various sizes to accomodate wounds of different sizes. A sufficiently large membrane 22 should normally be selected to provide ample overlap of the perimeter 26 over the healthy skin 16 to insure a good bond therebetween.

The tube distal end opening 39 may be placed directly over the approximate center of the wound site 12, or it may be placed eccentrically or at a depending location with respect to the wound site 12. A dependent or lower position for the opening 39 with respect to the wound site 12 may be preferred to facilitate fluid drainage. The dressing 10 may be applied promptly after a wound is inflicted, e.g. immediately after the graft removal procedure and a skin graft operation. To reduce the risk of infection, it may be advisable to promptly cover the open wound site 12. The wound dressing 10 may be kept in a sterile package until it is needed. Such sterile packages and packaging techniques are well known. For example, ethylene oxide may be used to sterilize the dressing 10 prior to placement in a suitable sterile package. The protective backing 23 is removed from the membrane 22, thereby exposing its adhesive-coated contact surface 28.

With the membrane 22 thus secured, a chamber 46 is formed between the wound site 12 and the membrane contact surface 28, and is surround by the membrane perimeter 26. The chamber 46 fluidically communicates with the membrane opening 32. In an evacuation mode of operation, such as might be desirable for forty-eight hours or so after removal of a split-thickness skin graft at a donor site, fluid 20 which accummulates in the chamber 46 is communicated through the opening 32 and thence through the tube 34 for collection and disposal. In a passive evacuation mode of operation, the fluid 20 is evacuated through capillary action, or by gravity with the opening 32 at a dependent, lower location in relation to the wound site 12. Such a capillary, passive drainage action may be sufficient for draining the wound site 12 in many situations. Alternatively, an active evacuation mode of operation involves attaching the tube 34 to the suction/vacuum source 42 whereby the fluid 20 is positively drawn from the wound site 12 and the chamber 46. Such an active evacuation mode of operation may be preferred when the dressing 10 is used in connection with a hydrophilic colloidal material (hydrocolloid), as will be explained in more detail hereinafter.

It may be desirable to operate the wound dressing 10 in an introduction mode of operation whereby medications such as antibiotics and growth factor solutions are introduced to the wound site 12. In this mode of operation, the tube distal end 38 is connected to a liquid solution source, which may comprise a syringe or any of various liquid containers for passive, gravity-induced introduction. Various adaptors, valves and injection needle ports are available for fluidically coupling the tube 34 to a wide variety of liquid solution sources. For example, many such connectors and adaptors are available from Aero International, Inc. of Reading, Pa. Such connecting devices are commonly used in connection with the intravenous introduction of various liquid solutions.

In an active introduction mode of operation, solutions may be pumped through the tube 34 into the chamber 46 for application to the wound site 12.

The evacuation and introduction treatment steps can be timed and sequenced as necessary to achieve the treatment objectives. For example, treatment of a skin graft donor site may involve fluid withdrawal and drainage for about two days immediately following the skin graft operation, followed by treatment steps comprising the introduction of antibiotics and/or growth factor solutions to the wound site. The evacuation and introduction steps can be alternated, and the intervals between such steps can be progressively increased or decreased as necessary to facilitate healing. As the wound heals, progressively smaller amounts of fluid will ooze therefrom and the frequency and duration of the drainage operations can be correspondingly reduced and finally discontinued altogether.

It will be appreciated that the wound dressing and treatment method of the present invention are broadly concerned with introducing fluid to wound sites and evacuating fluid therefrom. The fluid introduction and evacuation procedures described herein can be performed indefinitely without having to change the dressing 10. The tube 34 cooperates with the membrane 22 to permit the same dressing 10 to be used for both procedures, which may be alternated as often as necessary. Infection risks and patient discomfort can be reduced by minimizing wound dressing changes.

The removal of toxins and bacteria from wounds is an important aspect of the fluid drainage phase of the healing process. The wound dressing of the present invention facilitates removal of serum and other secretions to minimize the risk of infecting the wound site and macerating the tissue thereat. Growth factor solutions can be important in promoting healing, and antibiotics can be important in preventing and treating infection. Hence, a comprehensive wound treatment can be implemented with the wound dressing and treatment method of the present invention.

The wound dressing 10 can be employed to irrigate a wound whereby fluid is introduced and then removed.

The operation of the wound dressing 10 is largely a matter of fluid mechanics, and the function of the wound dressing 10 would probably be determined by such factors and variables as: (1) fluid viscosity; (2) permeability of the membrane 22; (3) cross-sectional area of the tube 34 and the area of its opening 39; (4) the integrity of the seal around the membrane perimeter 26; (5) the drawing power of the suction or vacuum source 42; (6) coagulation of the serum or other fluid; (7) the area of the fluid collection chamber 46; (8) the length of the tube 34; and (9) gravity and the relative positions of various components. Naturally, varying one or more of these factors or variables could change the operation of the system. It is anticipated that, applying such well-known principles of fluid mechanics, all of the wound dressing components could be properly sized and designed. For example, the tube opening 39 could be enlarged, or multiple openings could be provided to increase the rate of fluid flow into the tube 34. The rate of fluid flow can further be increased by locating the tube distal end 38 at a lower area within the chamber 46, i.e. below the level of most of the wound site 12. The tube 34 can extend downwardly to a collection site below the level of the wound site 12 to facilitate gravity drainage.

It is further anticipated that some fluids will resist drainage because of their viscosities or because they tend to coagulate. Drainage of such fluids can be effected by irrigating the wound site 12.

IV. First Modified Embodiment 110.

FIG. 8 shows a wound dressing 110 comprising a first modified embodiment of the present invention wherein a relatively small membrane 122 is provided and functions as a patch for a larger wound cover 115 with an opening 117 for receiving a distal end 138 of a tube 134. The primary wound cover 115 is selected to cover a wound site 112, and is placed thereover in the normal fashion. The wound dressing 110 can be placed on the primary wound cover 115 in a location chosen to enhance fluid introduction and/or evacuation. For example, to enhance the evacuation of fluid by gravity, it may be desirable to form the opening 117 at a relatively low position of the wound site 112. Thus, fluid will tend to flow to the tube 134 by gravity. To facility the introduction and distribution of fluid, it may be desirable to locate the wound dressing 110 at a relatively high position on the wound cover 115. In fact, two or more wound dressings 110 could be placed on a single, primary wound cover 115, with a lower wound dressing 110 being provided for fluid evacuation and an upper wound dressing 110 being provided for fluid introduction.

In the practice of the treatment method of the present invention, the wound dressing 110 provides for considerable flexibility in locating the wound dressing 110 in an appropriate location on the wound site 112. After the primary wound cover 115 is positioned, the opening 117 is formed at the chosen location and the wound dressing 110 may be applied, much like a patch, with the tube distal end 138 extending through the primary wound covery opening 117. It will be appreciated that wound dressings 110 may be changed as needed without changing the primary wound cover 115.

V. Second Modified Embodiment 210.

A wound dressing 210 comprising a second modified embodiment of the present invention is shown in FIGS. 9 and 10 and includes an intermediate layer of material 250 between a wound site 212 and a cover membrane 222. The intermediate material layer 250 can comprise a variety of materials with varying properties such as: (1) absorbency; (2) wicking or capillary action; and (3) surface contact action. The intermediate material layer is primarily located in a chamber 146 formed between the wound 212 and the membrane 222.

As a first example of an intermediate material layer 250, several hydrophilic colloid materials (i.e. hydrocolloids) are available which would tend to absorb fluids. For example, Envisan wound cleaning pads and paste are available from Marion Laboratories, Inc. of Kansas City, Mo. and comprise: spherical, hydrophilic Beads of Dextranomer, 0.1 to 0.3 mm in diameter; polyethylene glycol 3000 in the pad; polyethylene glycol 600; and water QS enclosed in a polyamide net bag in the pad or available in a metal foil packet for the paste. The Envisan dextraminer beads function to absorb fluid and facilitate healing by drawing fluid from the wound. Excess fluid can be drained from the intermediate material layer 250 to prolong its effectiveness. Other hydrocolloids are commercially available and may be employed with the wound dressing 210 of the present invention, e.g. dextranimers available under the trademark "Debrisan".

Alternatively, the intermediate material layer 250 can comprise a mesh or sheet of synthetic material which is generally nonabsorbent and would tend to wick fluid from the wound site 212 to a tube distal end 238. For example, rayon could be used to form such an intermediate material layer 250, and material available from Marion Laboratories, Inc. under the trademark "Envinet" could also be employed. Such materials may be referred to as "surface active", i.e. promoting fibrin sealing on the wound surface. Such materials can also satisfy a capillary purpose whereby fluid is wicked from the wound for collection in the chamber 246 and ultimately for drainage. With many such materials, a balance is struck between surface action and capillary action, i.e. one such function is often maximized at the expense of the other. For example, Owens rayon is generally considered to be relatively surface active, but may provide less capillary action than other materials. Envinet mesh, on the other hand, provides greater capillary action, but may provide less surface action as compared to the rayon material.

Other materials that can be used for the intermediate material layer 250 include polyurethane foam and polyurethane mesh.

The wound dressing 210 can be used according to methods for use with the other wound dressings 10 and 110, and includes the additional step of placing the intermediate material layer 250 over the wound site 212. It will be appreciated that there may be a number of materials suitable for the intermediate layer 250 to achieve various objectives.

A closure patch 251 is provided for placement over the tube distal end 238 and is adapted for securing it in a folded configuration to the membrane 222. The closure patch 251 can be used in conjunction with a bifurcated clip 240 as shown in FIGS. 9 and 10, and permits convenient access to the tube distal end 238 for coupling it to various devices such as those described herein.

It is to be understood that while certain forms of the present invention have been illustrated and described herein, it is not to be limited to the specific forms or arrangement of parts described and shown.

I claim:
1. A wound dressing, which includes:
(a) wound covering means with a skin contact surface and an outer surface;
(b) means for releaseably attaching said wound covering means to a patient in covering relation over a wound;
(c) said wound covering means having an interior portion with an opening extending between and open at the skin contact and outer surfaces thereof;
(d) said wound covering means comprising a semipermeable material; and
(e) tube means having a proximate end extending through said opening and terminating adjacent said skin contact surface and a distal end located outwardly from said outer surface, said tube means fluidically communicating with said skin contact surface.
2. The dressing according to claim 1 wherein:
(a) said tube proximate end is connected to said covering means at said opening thereof.
3. The dressing according to claim 1 wherein:

(a) said fastening means comprises adhesive on said skin contact surface at said perimeter portion.

4. The dressing according to claim 1 wherein:
(a) said wound covering means comprises semi-permeable plastic.

5. The dressing according to claim 1, which includes:
(a) an intermediate material layer adapted for placement between said cover means interior portion and said wound.

6. The dressing according to claim 5 wherein:
(a) said intermediate material is hydrocoloid.

7. The dressing according to claim 5 wherein:
(a) said intermediate material is nonabsorbant.

8. The dressing according to claim 5 wherein:
(a) said intermediate material includes a fibrin coating adapted for contacting the wound.

9. The dressing according to claim 5, wherein:
(a) said intermediate material includes a hydrocolloid and a nonabsorbant fabric sheet.

10. The dressing according to claim 1, which includes:
(a) means for closing said tube means distal end.

11. The dressing according to claim 10 wherein:
(a) said tube closing means comprises a clip.

12. The dressing according to claim 10, wherein said tube closing means comprises:
(a) a needle vent adapted for puncturing by an injection needle and adapted for resealing after the withdrawal thereof.

13. The dressing according to claim 10, which includes:
(a) suction means connected to said tube distal end.

14. The dressing according to claim 10 wherein:
(a) said tube proximate end is closed; and
(b) said tube includes an opening in spaced proximity to its proximate end.

15. The dressing according to claim 10, which includes:
(a) introduction means adapted for introducing liquid medication into said tube through its distal end.

16. A wound dressing, which includes:
(a) wound covering means including:
 (1) first and second panels each having a perimeter and an edge;
 (2) each said panel having an inner contact surface and an outer surface;
 (3) a seam extending transversely across said dressing and extending outwardly from said outer surface of said panels, said seam comprising said panels being connected together at their respective contact surfaces adjacent to their respective edges, said seam having opposite ends; and
 (4) a tube opening through said seam between said panel contact surfaces and intermediate said seam ends, said tube opening extending between and open at said adjacent perimeter edges and said contact surface;
(b) an adhesive coating on said panel contact surfaces; and
(c) a tube including proximate and distal ends, said tube extending through said tube opening and terminating adjacent said skin contact surface adjacent to its proximate end with said tube proximate end being positioned adjacent to said contact surface.

17. A wound dressing, which includes:
(a) wound covering means with a skin contact surface and an outer surface;
(b) means for releaseably attaching said wound covering means to a patient in covering relation over a wound;
(c) said wound covering means having an interior portion with an opening extending between and open at the skin contact and outer surfaces thereof;
(d) said wound covering means comprising a semi-permeable material; and
(e) tubular connector means having a proximate end extending through said opening and terminating adjacent said skin contact surface and a distal end located outwardly from said outer surface, said tubular connector means fluidically communicating with said skin contact surface and comprising a flexible, collapsible material.

18. A wound dressing, which includes:
(a) wound covering means including:
 (1) first and second panels each having a perimeter and an edge strip demarcated by a fold line, each said edge strip being folded outwardly from a remainder of a respective panel;
 (2) each said panel having an inner contact surface and an outer surface;
 (3) a seam extending transversely across dressing and extending outwardly from said outer surfaces of said panels, said seam comprising said edge strips being connected together at their respective contact surfaces, said seam having opposite ends; and
 (4) a tube opening extending through said seam between said edge strips and intermediate said seam ends, said tube opening extending between and open at said panel perimeters adjacent to said edge strips and said contact surface;
(b) an adhesive coating on said panel contact surfaces; and
(c) a tubular connector including proximate and distal ends, said tubular connector extending through said tube opening adjacent to its proximate end with said tube proximate end being positioned and terminating adjacent to said contact surface, said tubular connector comprising a flexible, collapsible material.

19. A method of dressing a wound surrounded by unwounded skin, which comprises the steps of:
(a) applying a semi-permeable covering comprising first and second panels each including a skin contact surface, an outer surface, and a perimeter with an edge over the wound.
(b) releaseably and adhesively attaching said skin contact surfaces of said panels to said unwounded skin around said wound;
(c) forming a seam with opposite ends and extending transversely across said covering by adhesively engaging said panel contact surfaces along respective strips adjacent to said edges thereof;
(d) providing an opening open at said perimeter edges and at said contact surface between said interconnected strips and intermediate said seam opposite ends;
(e) extending a tube with open proximate and distal ends through said tube opening;
(f) positioning said tube proximate end adjacent to said seam and said skin contact surface; and
(g) alternately introducing a liquid to and draining said wound through said tube.

20. The method of claim 19 wherein said step of introducing a liquid to said wound includes introducing liquid medication to said wound.

21. The method of claim 19 wherein said step of introducing a liquid to said wound includes irrigating said wound.

* * * * *

(12) EX PARTE REEXAMINATION CERTIFICATE (7017th)
United States Patent
Zamierowski

(10) Number: US 4,969,880 C1
(45) Certificate Issued: Aug. 25, 2009

(54) WOUND DRESSING AND TREATMENT METHOD

(75) Inventor: David S. Zamierowski, Leawood, KS (US)

(73) Assignee: Citibank, N.A., as Administrative Agent, New Castle, DE (US)

Reexamination Request:
No. 90/010,030, Oct. 1, 2007

Reexamination Certificate for:
| | |
|---|---|
| Patent No.: | 4,969,880 |
| Issued: | Nov. 13, 1990 |
| Appl. No.: | 07/332,699 |
| Filed: | Apr. 3, 1989 |

(51) Int. Cl.
*A61F 13/00* (2006.01)

(52) U.S. Cl. .................................. 604/305; 604/180
(58) Field of Classification Search ............... 604/543, 604/289–316, 167.02, 262
See application file for complete search history.

(56) References Cited

U.S. PATENT DOCUMENTS

| | | | | |
|---|---|---|---|---|
| 3,288,140 | A | * 11/1966 | McCarthy | 604/289 |
| 3,367,332 | A | * 2/1968 | Groves | 604/290 |
| 4,382,441 | A | 5/1983 | Svedman | |
| 4,920,970 | A | * 5/1990 | Wyatt | 600/486 |
| 4,969,880 | A | 11/1990 | Zamierowski | |

OTHER PUBLICATIONS

Wooding–Scott, M. et al., "No Wound is Too Big for Resourceful Nurses, Combining an Occlusive Transparent Dressing and a Suction System Meant Greater Patient Comfort and a Better Way to Treat the Wound," RN, Dec. 1988, pp. 22–25.

Svedman, P. et al., A Dressing System Providing Fluid Supply and Suction Drainage Used for Continuous or Intermittent Irrigation, Annals of Plastic Surgery, Aug. 1986, pp. 125–133, vol. 17, No. 2.

* cited by examiner

*Primary Examiner*—Catherine S. Williams

(57) ABSTRACT

A wound dressing includes a cover membrane comprising a semi-permeable material with an adhesive-coated skin contact surface. An opening is formed in an interior portion of the membrane. An intermediate layer of material may be placed between the wound and the membrane contact surface for either absorbing fluids from the wound, e.g. with a hydrocolloid or hydrophilic material, or for passing such fluids to the opening with a synthetic material, e.g. rayon. A tube includes a proximate end fluidically communicating with the wound through the membrane opening. A distal end of the tube is adapted for connection to a suction source for draining the wound or fluid source for introducing liquid medication to the wound. Both evacuation and introduction can be either active or passive. A wound treatment method is also disclosed.

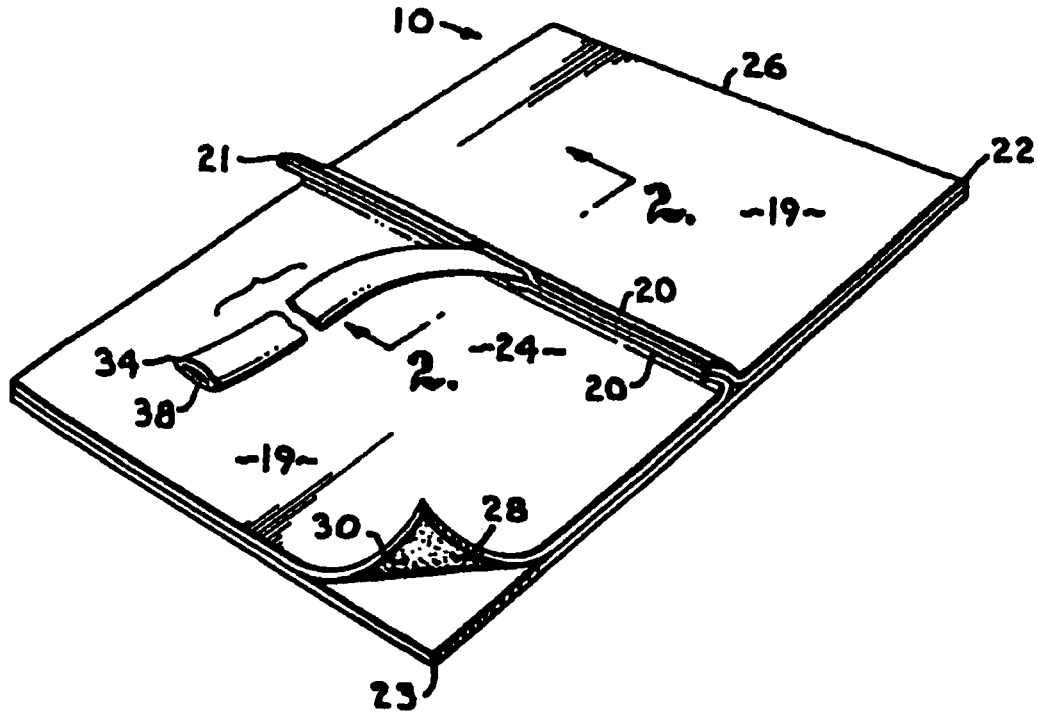

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–5, 7, 10–13, 15 and 17 are cancelled.

Claims 6, 8–9, 14, 16 and 18–21 were not reexamined.

\* \* \* \* \*